(12) United States Patent
Bae et al.

(10) Patent No.: US 9,040,917 B2
(45) Date of Patent: May 26, 2015

(54) EFFICIENT DATA EXTRACTION METHOD FOR HIGH-TEMPORAL-AND-SPATIAL-RESOLUTION NEAR INFRARED SPECTROSCOPY SYSTEM

(71) Applicant: Korea Advanced Institute of Science and Technology, Daejeon (KR)

(72) Inventors: Hyeon Min Bae, Seoul (KR); Jong-Kwan Choi, Daejeon (KR); Min-Gyu Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 311 days.

(21) Appl. No.: 13/744,339

(22) Filed: Jan. 17, 2013

(65) Prior Publication Data
US 2013/0256533 A1    Oct. 3, 2013

Related U.S. Application Data

(60) Provisional application No. 61/617,807, filed on Mar. 30, 2012.

(51) Int. Cl.
| | |
|---|---|
| *G01J 5/02* | (2006.01) |
| *G01J 3/28* | (2006.01) |
| *A61B 5/1455* | (2006.01) |
| *G01N 21/359* | (2014.01) |

(52) U.S. Cl.
CPC ............. *G01J 3/28* (2013.01); *G01N 21/359* (2013.01); *A61B 5/14553* (2013.01)

(58) Field of Classification Search
CPC .......................................................... G01J 3/28
USPC .................................................... 250/339.02
See application file for complete search history.

(56) References Cited

U.S. PATENT DOCUMENTS

| | | | | |
|---|---|---|---|---|
| 5,170,056 A | * | 12/1992 | Berard et al. | ............... 250/341.2 |
| 6,353,226 B1 | * | 3/2002 | Khalil et al. | ............... 250/341.8 |

* cited by examiner

*Primary Examiner* — David Porta
*Assistant Examiner* — Gisselle Gutierrez
(74) *Attorney, Agent, or Firm* — Blakely, Sokoloff, Taylor & Zafman LLP

(57) ABSTRACT

An efficient method for the extraction of hemodynamic responses in Near-Infrared Spectroscopy (NIRS) systems is proposed to increase the spatial and temporal resolution without hardware overhead. The performance improvement is attributed to high Signal-to-Noise-Ratio (SNR) receivers, a modulation scheme, and a Multi-Input-Multi-Output (MIMO) based data extraction algorithm. The proposed system shows an over 2x increment in the figure of merit (FOM) compared to conventional designs. Experimental results support the validity of the proposed system.

12 Claims, 15 Drawing Sheets

Light Way

US 9,040,917 B2

EFFICIENT DATA EXTRACTION METHOD FOR HIGH-TEMPORAL-AND-SPATIAL-RESOLUTION NEAR INFRARED SPECTROSCOPY SYSTEM

CROSS-REFERENCE TO RELATED APPLICATION

The present application is a U.S. nonprovisional application that claims priority to U.S. provisional application No. 61/617,807, filed Mar. 30, 2012, which is hereby incorporated by reference.

BACKGROUND OF THE INVENTION

1. Field of the Invention

Exemplary embodiments of the present invention relate to an efficient data extraction method for high-temporal-and-spatial-resolution near infrared spectroscopy (NIRS) system.

2. Discussion of the Background

There exist various functional brain imaging techniques, including functional magnetic resonance imaging (fMRI) and electroencephalography (EEG). The fMRI detects the hemodynamics of a functional brain and the EEG detects electrical signals induced from neural activities. The fMRI is known to be the best means for interpreting neural activity, despite two disadvantages: poor temporal resolution and limited portability. The portability is one of the important aspects in the brain imaging system in order to detect hemodynamics in dynamic condition. Then it is possible to find out the corresponding brain regions even in more generous situation, such as driving and face to face conversation.

SUMMARY OF THE INVENTION

An exemplary embodiment of the present invention discloses a near infrared spectroscopy (NIRS) system comprises a plurality of sources, each of the sources configured to emit a light and a plurality of detectors, each of the detectors configured to detect the light, wherein the sources and the detectors form a plurality of first hexagonal subsets, each of the first hexagonal subsets having one source at a center and six detectors at hexagonal vertexes, and two hexagonal vertex are shared between neighboring first hexagonal subsets.

The sources and the detectors form a plurality of unit hexagonal subsets (UHSs), each of the UHSs having a first hexagonal subset and a second hexagonal subset, and the second hexagonal subset overlapped in a portion of the first hexagonal subset by having one detector among the six detectors at a center of the second hexagonal subset.

Hemodynamic absorption coefficients of regions between the one detector corresponding to the center of the second hexagonal subset and detectors corresponding to vertexes of the second hexagonal subset, is calculated based on variations of optical densities of lights passed through region of the center of the second hexagonal subset.

The lights passed through region of the center of the second hexagonal subset, emitted from sources corresponding to vertexes of the second hexagonal subset.

The variations is calculated using a photon path length corresponding to the regions where the lights passed through and a differential pathlength factor (DPF) being different according to a penetrating medium of the regions.

The plurality of sources emit the light using code division multiple access (CDMA) scheme.

An exemplary embodiment of the present invention discloses a data extraction method for a near infrared spectroscopy (NIRS) system, the method comprises first operating a plurality of sources to emit lights and second operating a plurality of detectors to detect the lights, wherein the sources and the detectors form a plurality of first hexagonal subsets, each of the first hexagonal subsets having one source at a center and six detectors at hexagonal vertexes, and two hexagonal vertex are shared between neighboring first hexagonal subsets.

An exemplary embodiment of the present invention discloses one or more non-transitory computer-readable storage media having stored thereon a computer program that, when executed by one or more processors, causes the one or more processors to perform acts that extract a data, comprises first operating a plurality of sources to emit lights and second operating a plurality of detectors to detect the lights, wherein the sources and the detectors form a plurality of first hexagonal subsets, each of the first hexagonal subsets having one source at a center and six detectors at hexagonal vertexes, and two hexagonal vertex are shared between neighboring first hexagonal subsets.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION

Figure 1A:
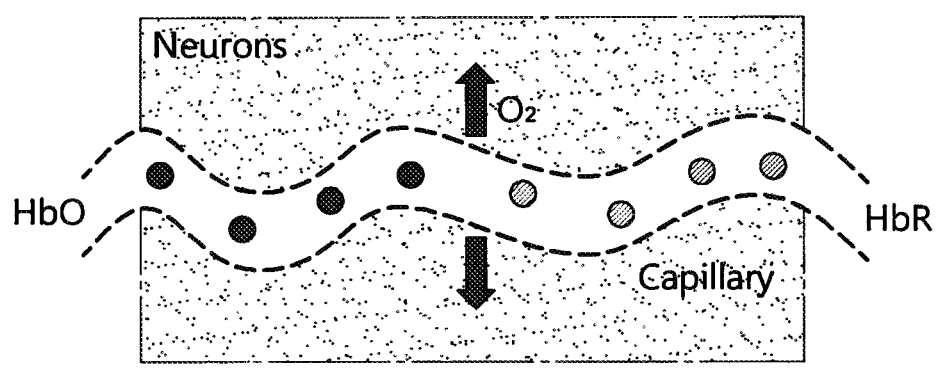
FIG. 1A shows the oxy-hemoglobin and deoxy-hemoglobin states in the steady state.

The invention is described more fully hereinafter with reference to the accompanying drawings, in which exemplary embodiments of the invention are shown. This invention may, however, be embodied in many different forms and should not be construed as limited to the embodiments set forth herein. Rather, these exemplary embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

I. INTRODUCTION

For decades, near-infrared spectroscopy (NIRS) has been widely used to monitor local changes in cerebral hemodynamics, which is caused by blood oxygenation and deoxygenation from functional brain activities. The difference in the near-infrared absorption spectra of oxyhemoglobin ($HbO_2$) and deoxy-hemoglobin (HbR) enables the separation of the concentrations of these two molecules. The NIRS requires relatively small equipment, so it offers a better portability than fMRI. Also, the NIRS has a better temporal resolution as millisecond range than fMRI. However, the NIRS has poor spatial resolution than fMRI and it is the main obstacle for its widespread use. Therefore, studies on the NIRS system have focused on improving its spatial resolution. The NIRS produces functional brain images by analyzing the hemodynamic responses measured from neighboring pairs of sources and detectors. The spatial resolution of the NIRS is determined by the distance between the source and detector (SD), which should be at least 2 cm, in order to detect the light passing deep into the cerebral layer. Therefore, the resolution of the conventional NIRS, in which a number of single channels SD are alternatively placed, is limited by the minimum separation requirement of the SD. An improvement in the spatial resolution can be achieved while sacrificing the temporal resolution by placing multiple SD pairs in a 3 cm region and alternatively extracting the data in the time domain.

In exemplary embodiments of the present invention, an efficient data extraction method is proposed for an increased spatial resolution in the NIRS without sacrificing the temporal resolution. The performance improvement is attributed to high signal-to-noise-ratio (SNR) receivers, a modulation scheme, and a MEMO-based data extraction algorithm.

II. BASIC THEORY OF NIRS

A. Cerebral Hemodynamics and NIR Light Property in the Head

Figure 1B:
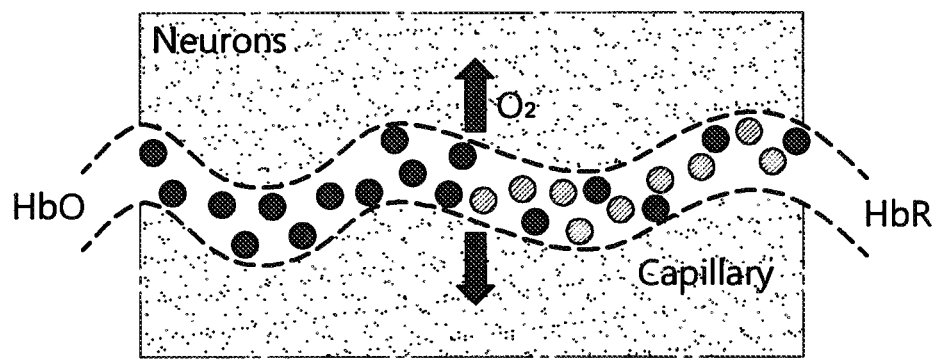
FIG. 1B shows the oxy-hemoglobin and deoxy-hemoglobin states when local neuronal activity takes place.

Neuronal activity is known to be associated with the changes of local cerebral blood flow and local cerebral blood volume in the arterial. Additionally, the variations in $HbO_2$ and HbR concentrations in the venous are occurred concurrently. These changes are referred to as cerebral hemodynamics which is described in FIG. 1A to FIG. 1B. FIG. 1A shows the oxy-hemoglobin and deoxy-hemoglobin states in the steady state and FIG. 1B shows the oxy-hemoglobin and deoxy-hemoglobin states when local neuronal activity take place.

Figure 2A:
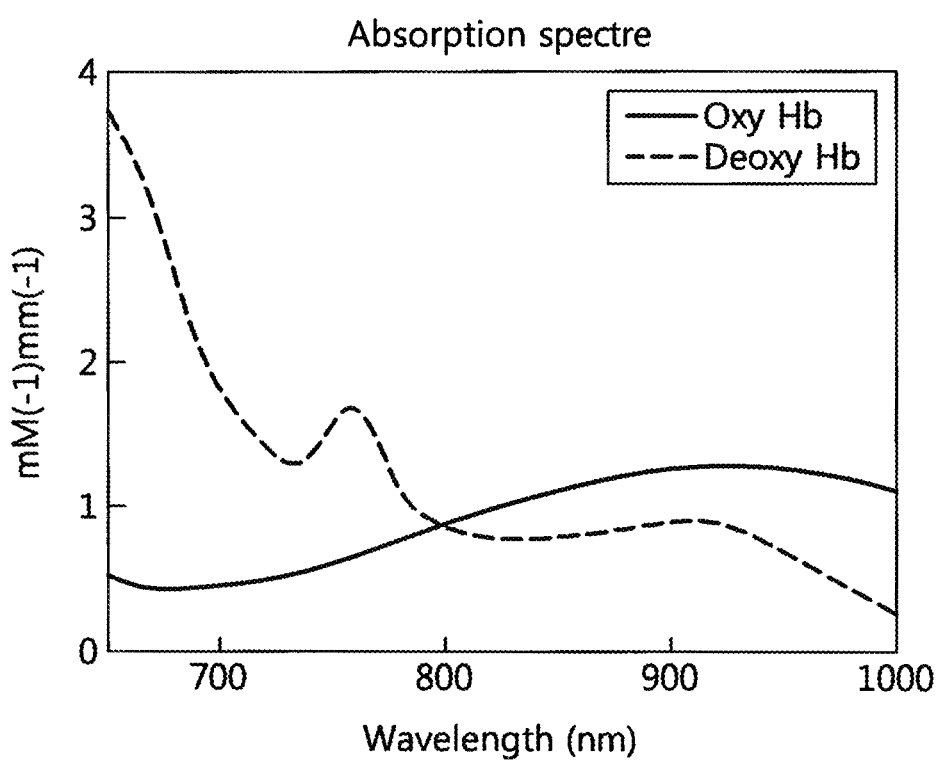
FIG. 2A shows the extinction spectra of $HbO_2$ and HbR in the near-infrared range.
Figure 2B:
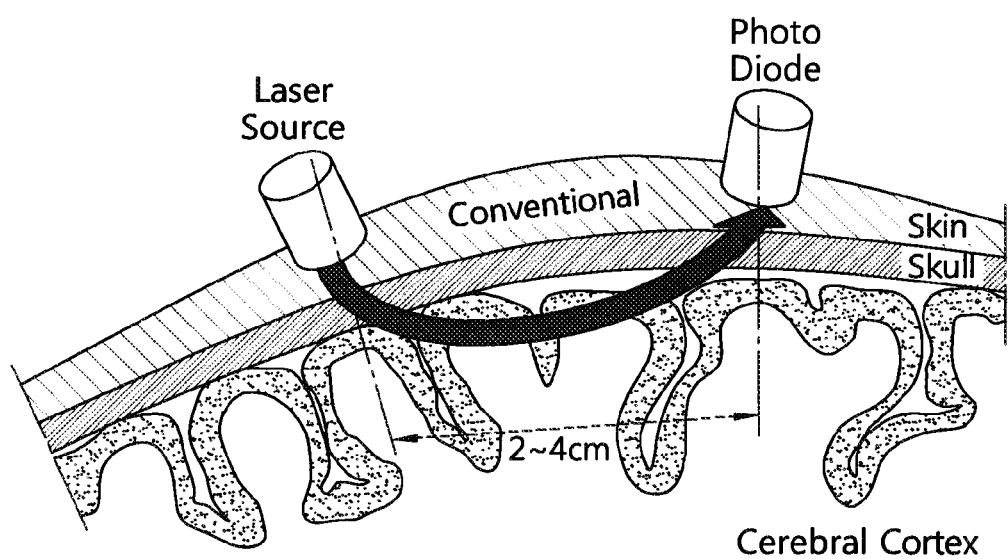
FIG. 2B shows the light penetrating path in the brain layers.

The NIRS is expected to detect such changes by using the properties of $HbO_2$ and HbR toward light. FIG. 2A shows the extinction spectra of $HbO_2$ and HbR in the near-infrared range. Conventional NIRS systems use the wavelength pairs that are symmetric with respect to the 800 nm to achieve the reverse extinction value of $HbO_2$ and HbR. The emitted light from a source propagates about 2 to 4 cm toward a detector in a banana shape through the brain channel, as shown in FIG. 2B. FIG. 2B shows the light penetrating path in the brain layers.

The channel is mainly composed of skin, skull, cerebral spinal fluid and cerebral cortex. As a result, the degree of absorption of the incident light in the activated cerebral cortex varies depending on the degree of hemodynamics.

B. Modified Beer-Lambert Law (MBLL)

The main governing equation for NIRS is the MBLL. It can be written from the following Equation 1.

$$\Phi(\lambda) = -\ln\frac{I_d}{I_e} = \epsilon CLP + G \qquad \text{[Equation 1]}$$

wherein $\Phi(\lambda)$ is the optical density of corresponding wavelength $\lambda$, $I_e$ is the emitted light intensity of the laser source, $I_d$ is the detected light intensity, $\epsilon$ is the extinction coefficient of the molecules ($cm^{-1}mm^{-1}$), C is the concentration of each molecule (mM) that organize the brain, L is the distance between the light source and the detector, P is a differential Pathlength Factor (DPF), which accounts for increases in the photon path length caused by tissue scattering, and G is a factor of geometry measurement of the detector.

The emitted light from a source is absorbed and scattered in the brain channel. The variation of channel characteristics, such a hemodynamics, causes the variation in detected optical signal power. In this case, the Equation 1 can be rewritten as the following Equation 2.

$$\begin{aligned}\Delta\Phi(\lambda, t_d) &= \Phi(\lambda, t_d) - \Phi(\lambda, t_i) \qquad \text{[Equation 2]}\\ &= -\ln\frac{I_d(\lambda, t_d)}{I_d(\lambda, t_i)}\\ &= (\epsilon_{HbO,\lambda}\Delta C_{HbO}(t_d) + \epsilon_{HbR,\lambda}\Delta C_{HbR}(t_d))LP_\lambda\end{aligned}$$

wherein $\Delta\Phi(\lambda, t_d)$ is the change in optical density from the detected time, $I_d$ to the initial time, $t_i$. The measured intensity variation contains hemodynamic information, such as the concentration variations of $\Delta C_{HbO_2}$ and $\Delta C_{HbR}$. The other molecules in brain layers at the wavelength range of 600 to 900 nm are water, liquids, and cytochrome aa3. However, their contribution is less significant than $HbO_2$ and HbR. Thus, this wavelength range is a suitable therapeutic window that can penetrate through the brain layers. The following Equation 3 is the MBLL equation that considers the contribution of oxy and deoxy hemoglobin where the $\lambda_1$ and $\lambda_2$ indicate a particular wavelength pair within this window. By measuring $\Delta\Phi$ at two wavelengths, and using the known extinction coefficients of $HbO_2$ and HbR at those wavelengths, the concentration changes of $HbO_2$ and HbR may be determined. The Equation 3 indicates the rearranged MBLL, which extracts the variations in the $HbO_2$ and HbR concentrations.

$$\begin{bmatrix} \Delta C_{HbO}(t_d) \\ \Delta C_{HbR}(t_d) \end{bmatrix} = \frac{1}{LP} \begin{bmatrix} \alpha_{HbO}(\lambda_1) & \alpha_{HbR}(\lambda_1) \\ \alpha_{HbO}(\lambda_2) & \alpha_{HbR}(\lambda_2) \end{bmatrix}^{-1} \times \begin{bmatrix} \Delta\Phi(\lambda_1, t_d) \\ \Delta\Phi(\lambda_2, t_d) \end{bmatrix} \quad \text{[Equation 3]}$$

III. HEMODYNAMICS EXTRACTION METHODOLOGIES

In the NIRS system, a SD pair operates together to extract the hemodynamic information of corresponding brain regions, as shown in FIG. 2B. Since the transmitted signal is known, while hemodynamics in the brain channel is unknown, so NIRS system should solve an inverse problem. The power scale of the detected light is in the order of a few nanowatts depending on the distance between SD. The detected hemodynamic information is weak against the outside noise caused by physical phenomena. Thus, in order to achieve a high SNR with improved spatial and temporal resolution, the joint optimization in the system architecture, algorithm and circuits was implemented in exemplary embodiments of the present invention.

The intensity of a near-infrared light decrease as it penetrates into the skull and the cerebral layers due to scattering and absorption. When a detector receives the signals from multiple laser sources with different path lengths simultaneously, the well-known near-far problem occurs. The near-far problem an be overcome if the dynamic range of the analog front-end (AFE) is sufficiently large so that the smallest signal has an adequate SNR for the extraction of the hemodynamics.

Figure 3A:
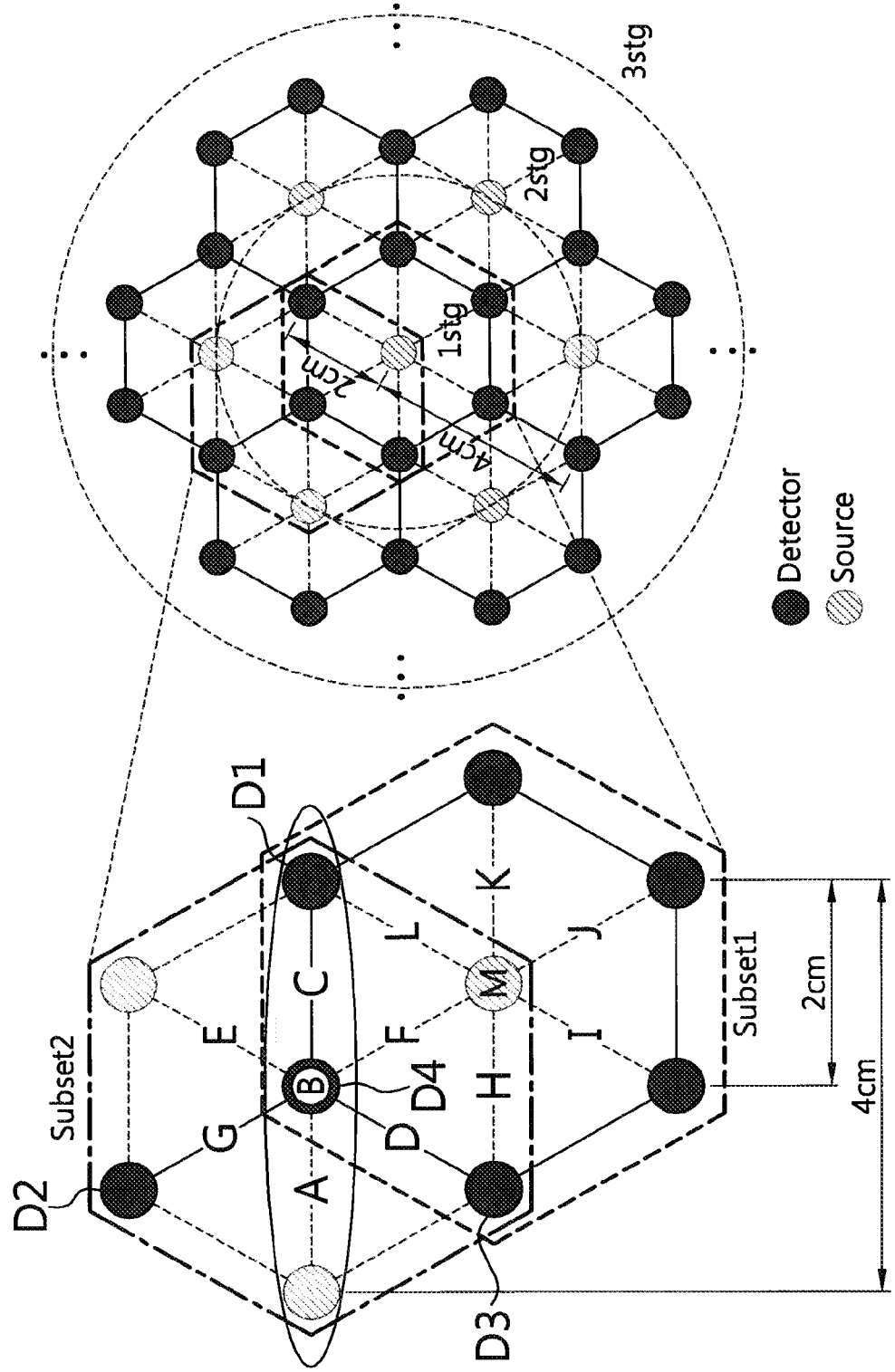
FIG. 3A shows the hexagonal SD array structure according to an exemplary embodiment of the present invention.

In conventional NIRS, a single hemodynamic response is extracted from a single pair of SD. In this case, the spatial resolution can be increased only by placing more SD pairs. However, the proposed approach incorporates a multi-input multi-output (MIMO) scheme for a hexagonal SD array structure that can increase the spatial resolution without hardware increment. FIG. 3A shows the hexagonal SD array structure according to an exemplary embodiment of the present invention. Subset 1 forms the basis of the structure called as the Unit Hexagonal Subset (UHS). The design goal is to detect the hemodynamics in the entire internal points, vertexes and edges of the UHS. Neighboring SDs may be separated by 2 cm. It is needed to define another subset to show how the hemodynamics at the vertex (B) and the edges (C, D, G) can be extracted. We drew an arbitrary hexagon, subset 2, as seen in FIG. 3A. Subset 2 has 3 sources and 3 detectors alternatively located at each hexagonal vertex and 1 detector at the center. Subset 1 has 6 detectors at the vertices and 1 source at the center. The distance between SD may be 2 cm.

The minimum distance of a SD pair may be 2 cm and the maximum may be 4 cm. The hexagonal structure has advantage of scalability as 1 stg, 2 stg, and 3 stg expanded repeatedly to cover the entire brain region.

The scalable UHS has been incorporated and combined with MIMO and code division multiple access (CDMA) schemes. The source separation is achieved by modulating the hemodynamics signal using the Walsh code. The Walsh code is perfectly orthogonal to other codes, allowing it to remove the interference, while the Pseudo-random Noise (PN) sequence of the conventional Code Modulation method is not. The Walsh code distribution has orthogonal patterns equal number of spread factor, i.e., the code length.

A. Light Propagation in UHS

Figure 3B:
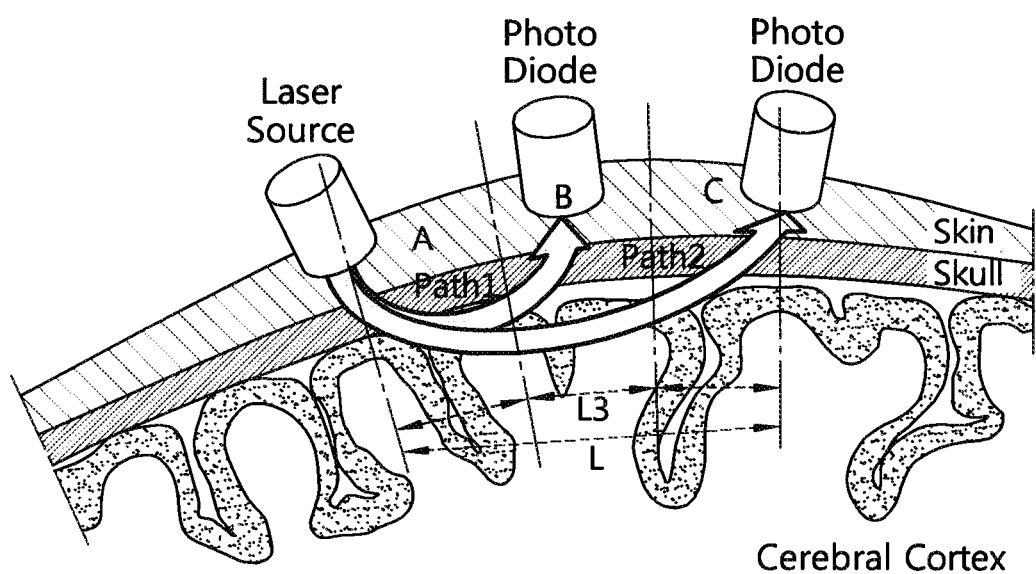
FIG. 3B shows the tentative light paths toward two photo diodes according to an exemplary embodiment of the present invention.

FIG. 3B shows the tentative light paths toward two photo diodes according to an exemplary embodiment of the present invention. Paths 1 and 2 indicate the pathway which SD separation is 2 cm and 4 cm, respectively. Light passing through path 1 contains the optical property of region A, while light passing through path 2 contains those of A, B and C simultaneously. The received optical power $I_d$ in path 2 can be described as the following Equation 4.

$$I_d = I_e \times \exp\left(-\epsilon C_A \frac{L}{3} P_A\right) \times \exp\left(-\epsilon C_B \frac{L}{3} P_B\right) \times \exp\left(-\epsilon C_C \frac{L}{3} P_C\right) \times \exp(-G) \quad \text{[Equation 4]}$$

wherein $C_A$, $C_B$ and $C_C$ are the hemoglobin concentrations in each region and $P_A$, $P_B$ and $P_C$ are DPFs in each region. The difference in the optical power $\Delta\Phi$ between time $t_d$ and $t_i$ in path 2 may be represented by the following Equation 5.

$$\begin{aligned} \Delta\Phi(\lambda) &= -\ln\frac{I_{d,t_d}}{I_{d,t_i}} \quad \text{[Equation 5]} \\ &= (\epsilon_{HbO,\lambda}\Delta C_{A,HbO}(t_d) + \epsilon_{HbR,\lambda}\Delta C_{A,HbR}(t_d))\frac{L}{3}P_{A,\lambda} + \\ &\quad (\epsilon_{HbO,\lambda}\Delta C_{B,HbO}(t_d) + \epsilon_{HbR,\lambda}\Delta C_{B,HbR}(t_d))\frac{L}{3}P_{B,\lambda} + \\ &\quad (\epsilon_{HbO,\lambda}\Delta C_{C,HbO}(t_d) + \epsilon_{HbR,\lambda}\Delta C_{C,HbR}(t_d))\frac{L}{3}P_{C,\lambda} \end{aligned}$$

wherein $\epsilon_{HbO,\lambda}$ and $\epsilon_{HbR,\lambda}$ denote the wavelength dependent extinction coefficients of oxy and deoxy hemoglobin, respectively and $\Delta C_{region,HbX}$ is the change in the concentrations of the molecule in a corresponding region. The light path through A, B and C is one of the channels in the UHS SD array as shown in FIG. 3A. The optical density variation in each region can be calculated by using the region extraction matrix in hexagonal model.

B. DPF Calculation of the Divided Sections in the UHS

Figure 4A:
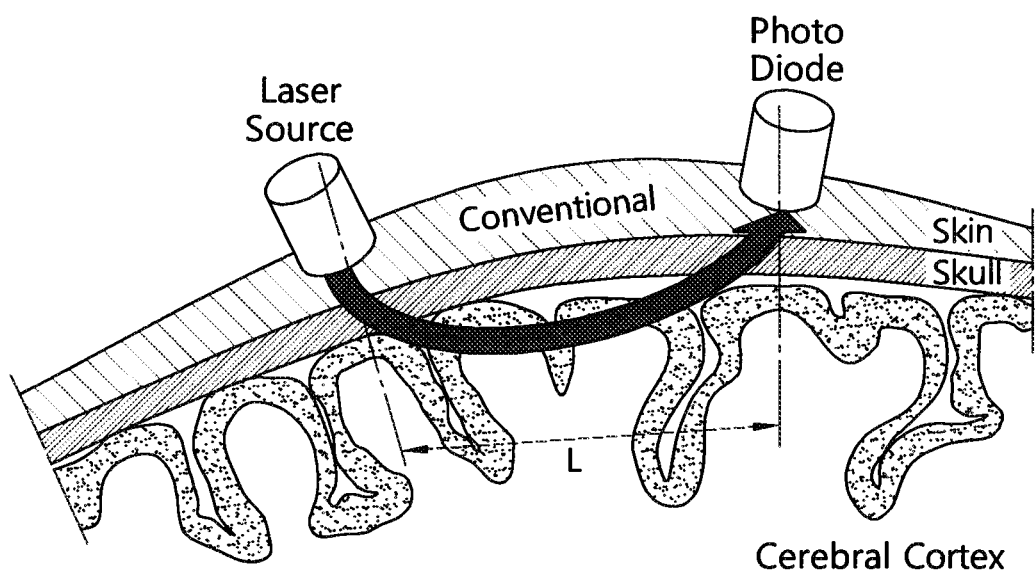
FIG. 4A shows conventional composition of brain channel.
Figure 4A:
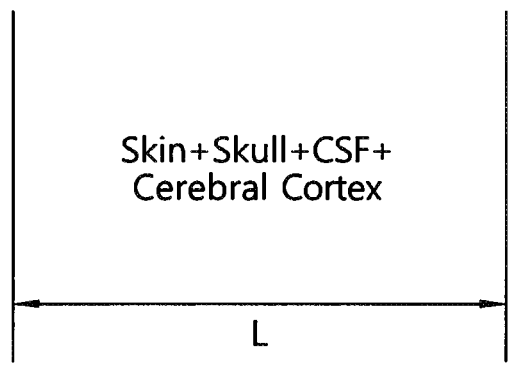
Figure 4B:
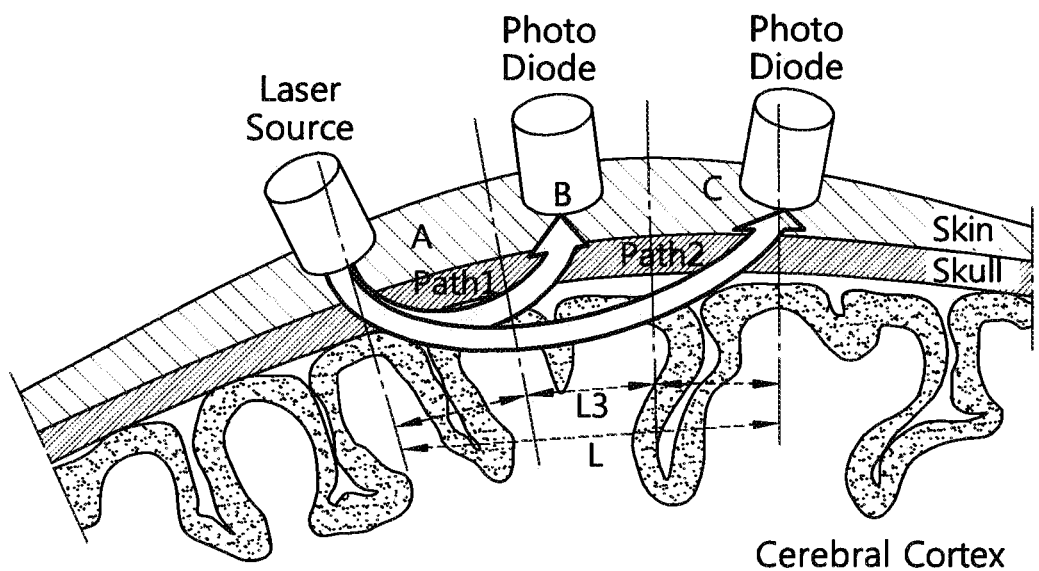
FIG. 4B shows separated composition of brain channel for hexagonal structure according to an exemplary embodiment of the present invention.
Figure 4B:
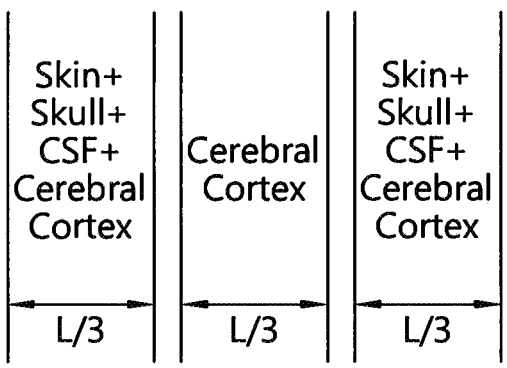

Absolute DPF cannot be acquired by the continuous wave (CW) based NIRS, which has simple structure, cheap price and suitable for continuous monitoring. It can detect only the measured optical density changes that reflect the changes in $HbO_2$ and HbR. If the changes of medium characteristic or structure occur, they will cause the errors about changes in $HbO_2$ and HbR concentration. Therefore, DPF is calculated with the assumption that the medium is homogeneous. However, in our hexagonal structure, the DPFs of each region A, B, and C in FIG. 4B are different since the DPF is a strong function of the penetrating medium. FIG. 4A shows conventional composition of brain channel, and FIG. 4B shows separated composition of brain channel for hexagonal structure according to an exemplary embodiment of the present invention.

An incident light penetrates into surface tissue layers, the skull, and cerebrospinal fluid (CSF) sequentially before reaching the cerebral cortex. The light paths in the regions A and C contain the skin, skull, CSF and cerebral cortex, while in the region B contains only the cerebral cortex layer is contained. Thus, the DPFs in regions A and C differ from that in region B. Therefore, the conventional condition should be modified because does not like its assumption, brain layers are inhomogeneous with a semi-infinite boundary as FIG. 4A, should be modified.

The appropriate DPFs are estimated by analyzing the light propagation under an infinite slab boundary condition. The diffuse photon fluence rate, which means photon density Φ(r, t), satisfies the diffusion equation as the following Equation 6.

$$\frac{1}{c}\frac{\partial}{\partial t}\Phi(r,t) - D\Delta^2\Phi(r,t) + \mu_a\Phi(r,t) = S(r,t) \quad \text{[Equation 6]}$$

wherein c is the speed of light in the tissue, S(r, t) is the photon source and D is the diffusion coefficient defined as the following Equation 7.

$$D\|=3[\mu_a+\mu'_s]^{-1} \quad \text{[Equation 7]}$$

wherein $\mu_a$ is absorption coefficient and $\mu'_s$ is scattering coefficient defined as $(1-g)\mu_s$. Those coefficients are the average of the characteristics of several layers composed medium, g is the mean cosine of the scattering angle.

Figure 5A:
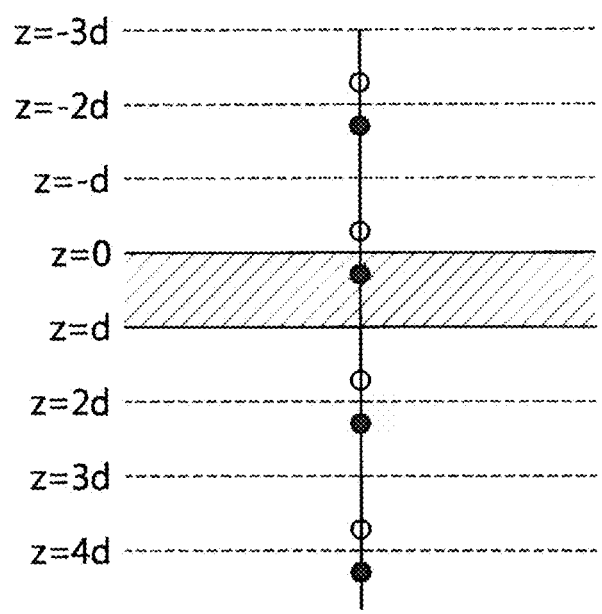
FIG. 5A shows geometry for the calculation of the time resolved reflectance and transmittance from a homogeneous slab.
Figure 5B:
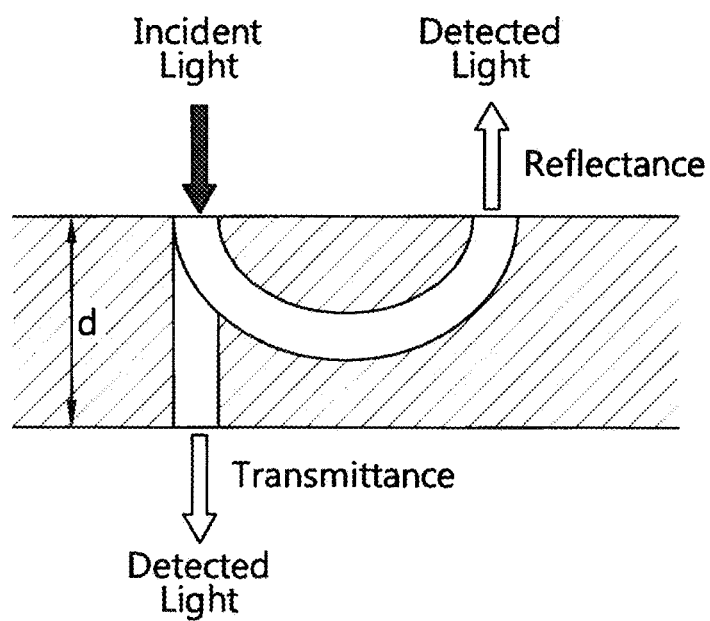
FIG. 5B shows the reflectance and transmittance pathway in a homogeneous slab medium.

The light propagation in turbid media has been analyzed in many studies. These studies have solved the temporal reflectance, R(ρ, t) and transmittance T(ρ,d, t) that are necessary to calculate DPF values with the modeling of geometry in slab boundary conditions, as shown in FIG. 5A and FIG. 5B. FIG. 5A shows geometry for the calculation of the time resolved reflectance and transmittance from a homogeneous slab, and FIG. 5B shows the reflectance and transmittance pathway in a homogeneous slab medium. (ρ, t) means that photons arrived in position ρ at time t, and d is the thickness of slab medium. The general form of the reflectance, R(ρ, t) induced from Equation 6 may be represented by the following Equation 8.

$$R(\rho, t) = (4\phi Dc)^{-3/2} z_0 t^{-5/2} \exp(-\mu_a ct) \exp\left(-\frac{\rho^2 + z_0^2}{4Dct}\right) \quad \text{[Equation 8]}$$

Also, DPF may be defined as the following Equation 9.

$$DPF = \frac{\langle L \rangle}{r} \cong \frac{\upsilon \langle t \rangle}{r} = \frac{\upsilon}{r}\frac{\int_0^\infty tR(\rho,t)dt}{\int_0^\infty R(\rho,t)dt} \quad \text{[Equation 9]}$$

wherein the average photon pathlength <L> is much larger than the SD distance. The light path of the hexagonal model is divided into 3 sections and each light path can be assumed as a slab medium. Thus, the transmittance is the output of the section, which is the same as the input of the next section. The spatially integrated transmittance penetrating to a finite tissue slab may be represented by the following Equation 10.

$$T(d, t) = (4\phi Dc)^{-3/2} z_0 t^{-5/2} e^{-\mu_a ct} \times \left[ (d-z_0)e^{\left(-\frac{(d-z_0)^2}{4Dct}\right)} - (d+z_0)\exp\left(-\frac{(d+z_0)^2}{4Dct}\right) + (3d-z_0)e^{\left(-\frac{(3d-z_0)^2}{4Dct}\right)} - (3d+z_0)e^{\left(-\frac{(3d+z_0)^2}{4Dct}\right)} \right] \quad \text{[Equation 10]}$$

Then the Equation 9 can be rewritten by the transmittance shown in the Equation 10, which is substituted for reflectance, as the following Equation 11.

$$DPF = \frac{\upsilon}{r}\frac{\int_0^\infty tT(\rho,t)dt}{\int_0^\infty T(\rho,t)dt} \quad \text{[Equation 11]}$$

We should determine the absorption and reduced scattering coefficient of medium to calculate DPFs. The coefficients, $\mu_a$, $\mu'_s$, are slightly changed when the wavelength is changed. Therefore, coefficients as those shown in the following Table 1 may be used.

TABLE 1

|  | 780 nm | | 850 nm | |
| --- | --- | --- | --- | --- |
|  | $\mu_a$ | $\mu_s$ | $\mu_a$ | $\mu_s$ |
| Scalp | 0.164 | 7.1 | 0.191 | 6.6 |
| Skull | 0.115 | 9.1 | 0.136 | 8.6 |
| Cerebralspinal Fluid | 0.017 | 0.1 | 0.026 | 0.1 |
| Gray matter | 0.17 | 11.6 | 0.186 | 11.1 |

In the conventional MBLL, the averaged coefficients of all layers, such as scalp, skull, CSF as shown in the following Table 2, and gray matter are used since the light penetrates all layers formed in the human head in the process of propagating each source to each detector.

TABLE 2

|  | 780 nm | | 850 nm | |
| --- | --- | --- | --- | --- |
|  | $\mu_a$ | $\mu_s$ | $\mu_a$ | $\mu_s$ |
| A, C (Scalp + Skull + CSF + Brain) | 0.117 | 6.98 | 0.135 | 6.6 |
| B (Gray matter) | 0.17 | 11.6 | 0.186 | 11.1 |

In the following Table III, the estimated DPF values in the regions A, C and B are 3.764 and 5.972 at a wavelength of 780 nm and 3.3 and 4.7 at a wavelength of 850 nm, respectively.

TABLE 3

|  | 780 nm | 850 nm |
| --- | --- | --- |
| A, C (Scalp + Skull + CSF + Brain) | 3.764 | 3.3 |
| B (Gray matter) | 5.972 | 4.7 |

Note that conventional DPFs are calculated with a semi-infinite boundary condition, which are 5.075 and 4.64 at wavelengths of 780 and 850 nm, respectively__ under a 2 cm SD separation.

C. MIMO Extraction Method for Hemodynamic Response

The subset 2 shown in FIG. 3A, the hemodynamic responses in 7 regions, such as A~G, should be extracted by using 4 detectors and 3 sources. It is possible, as shown in the following Equation 12 to interpret the detected optical density variations that contain hemodynamic information of corresponding regions where $L_{div}$ is L/3. Detectors, such as D1, D2, and D3, receive signals from laser sources separated by both 2 cm and 4 cm simultaneously. By measuring the optical density variation $\Delta\Phi_{D,4\,cm}(\lambda)$ at two wavelengths and using the known extinction coefficients of oxy and deoxy hemoglobin ($\epsilon_{HbO,\lambda}$, $\epsilon_{Hbr,\lambda}$) at those wavelengths, we can determine the concentration changes of oxy and deoxy hemoglobin ($\Delta C_{Region,HbO}$, $\Delta C_{Region,HbR}$) in each region D1 detects the light that penetrates the A, B and C regions, D2 detects the light that passes through F, B and G and D3 detects the light penetrating through E, B and D regions.

$$\Delta\Phi_{D1,4cm}(\lambda) = -\ln\frac{I_{dectected-time,\lambda,D1}}{I_{initial-time,\lambda}} = \quad \text{[Equation 12]}$$
$$(\epsilon_{HbO,\lambda}\Delta C_{A,HbO} + \epsilon_{HbO,\lambda}\Delta C_{A,HbO})L_{div}P_{A,\lambda} +$$
$$(\epsilon_{HbO,\lambda}\Delta C_{B,HbO} + \epsilon_{HbO,\lambda}\Delta C_{B,HbO})L_{div}P_{B,\lambda} +$$
$$(\epsilon_{HbO,\lambda}\Delta C_{C,HbO} + \epsilon_{HbO,\lambda}\Delta C_{C,HbO})L_{div}P_{C,\lambda},$$

$$\Delta\Phi_{D2,4cm}(\lambda) = -\ln\frac{I_{dectected-time,\lambda,D2}}{I_{initial-time,\lambda}} =$$
$$(\epsilon_{HbO,\lambda}\Delta C_{F,HbO} + \epsilon_{HbO,\lambda}\Delta C_{F,HbO})L_{div}P_{F,\lambda} +$$
$$(\epsilon_{HbO,\lambda}\Delta C_{B,HbO} + \epsilon_{HbO,\lambda}\Delta C_{B,HbO})L_{div}P_{B,\lambda} +$$
$$(\epsilon_{HbO,\lambda}\Delta C_{G,HbO} + \epsilon_{HbO,\lambda}\Delta C_{G,HbO})L_{div}P_{G,\lambda},$$

$$\Delta\Phi_{D3,4cm}(\lambda) = -\ln\frac{I_{dectected-time,\lambda,D3}}{I_{initial-time,\lambda}} =$$
$$(\epsilon_{HbO,\lambda}\Delta C_{E,HbO} + \epsilon_{HbO,\lambda}\Delta C_{E,HbO})L_{div}P_{E,\lambda} +$$
$$(\epsilon_{HbO,\lambda}\Delta C_{B,HbO} + \epsilon_{HbO,\lambda}\Delta C_{B,HbO})L_{div}P_{B,\lambda} +$$
$$(\epsilon_{HbO,\lambda}\Delta C_{D,HbO} + \epsilon_{HbO,\lambda}\Delta C_{D,HbO})L_{div}P_{D,\lambda}$$

Let the hemodynamic absorption coefficient $A_{Hemo,\lambda}(X)$ be $\epsilon_{HbO,\lambda}\Delta C_{X,HbO}\epsilon_{HbR,\lambda}\Delta C_{X,HbR}$.

The following Equation 13 shows the variations in the optical power density. The signals from the source apart from the detector, such as 4 cm, can be separated and extracted as the following Equation 13 via demodulation method.

$$\Delta\Phi_{D1,4\,cm}(\lambda) = A_{Hemo,\lambda}(A)L_{div}P_{A,\lambda} + A_{Hemo,\lambda}(B)L_{div}P_{B,\lambda} + A_{Hemo,\lambda}(C)L_{div}P_{C,\lambda},$$

$$\Delta\Phi_{D2,4\,cm}(\lambda) = A_{Hemo,\lambda}(F)L_{div}P_{F,\lambda} + A_{Hemo,\lambda}(B)L_{div}P_{B,\lambda} + A_{Hemo,\lambda}(G)L_{div}P_{G,\lambda},$$

$$\Delta\Phi_{D3,4\,cm}(\lambda) = A_{Hemo,\lambda}(E)L_{div}P_{E,\lambda} + A_{Hemo,\lambda}(B)L_{div}P_{B,\lambda} + A_{Hemo,\lambda}(D)L_{div}P_{D,\lambda} \quad \text{[Equation 13]}$$

The detector D4 may directly detect the hemodynamic responses in regions A, F, and E simultaneously from laser sources separated by 2 cm. Since the region B is surrounded by 6 regions separated only by 1 cm, we interpolated the hemodynamics of the surrounding regions linearly to achieve that of region B, as given by the following Equation 14.

$$A_{Hemo,\lambda}(B) = \quad \text{[Equation 14]}$$
$$\frac{1}{6}(A_{Hemo,\lambda}(A) + A_{Hemo,\lambda}(C) + A_{Hemo,\lambda}(D) + A_{Hemo,\lambda}(E) + A_{Hemo,\lambda}(F) + A_{Hemo,\lambda}(G))$$

From the Equation 13 and the Equation 14, the unknown hemodynamics in regions C, D, and G can be extracted as given by the following Equation 15.

$$\begin{bmatrix} A_{Hemo,\lambda}(C) \\ A_{Hemo,\lambda}(G) \\ A_{Hemo,\lambda}(D) \end{bmatrix} = \quad \text{[Equation 15]}$$
$$\frac{1}{P'P_{eq}}L_{div}\begin{bmatrix} P_{eq}-P'' & -P'' & -P'' \\ -P'' & P_{eq}-P'' & -P'' \\ -P'' & -P'' & P_{eq}-P'' \end{bmatrix} \times$$

$$\begin{bmatrix} \Delta\Phi_{D1,4cm}(\lambda) \\ \Delta\Phi_{D2,4cm}(\lambda) \\ \Delta\Phi_{D3,4cm}(\lambda) \end{bmatrix} - \begin{bmatrix} A_{Hemo,\lambda}(A) \\ A_{Hemo,\lambda}(F) \\ A_{Hemo,\lambda}(E) \end{bmatrix}$$

where P' and P'' denote the DPF in regions A and B in FIG. 3, respectively, and $P_{eq}=6P''+3P''$ P is the same value as $P_{A,\lambda}$, $P_{C,\lambda}$, $P_{D,\lambda}$, $P_{E,\lambda}$, $P_{F,\lambda}$, $P_{G,\lambda}$ which are the DPF when the light penetrates all layers from skin to the brain with 4/3 cm length. The value is shown in the Table 3 as 3.764 for 780 nm and 3.3 for 850 nm. P''' is the same as $P_{B,\lambda}$ which is the DPF where the light passes only the brain layer in the same length. As P', P''' value is also shown in the following Table 3 as 5.972 for 780 nm and 4.7 for 850 nm. In the subset 1, the hemodynamics in 6 regions such as F~L without G can be detected directly and the center region M can be interpolated as that in the Equation 14. The following Table4 categorizes and counts the number of detection regions when the number of UHS stages is expanded to several stages.

TABLE 4

| Detecting point | In FIG. 1(A) | General Equation of # of Detecting Points (n = stage) |
|---|---|---|
| The center region of SD separated (2 cm) | A, E, F, H, I, J, K, L | $6(3n^2 - 3n + 1)$ |
| The edges of UHS | G, C, D | $6n^2$ |
| The center region of UHS | M | $3n^2 - 3n + 1$ |
| The vertex region of UHS | B | $6(n-1)^2$ |

In the n stage hexagonal structure, the general equations of the total number of used sources and detectors are $3n^2-3n+1$ and $6n^2$, respectively. As a result, we have achieved 1 cm spatial resolution through the MIMO extraction method.

Figure 6A:
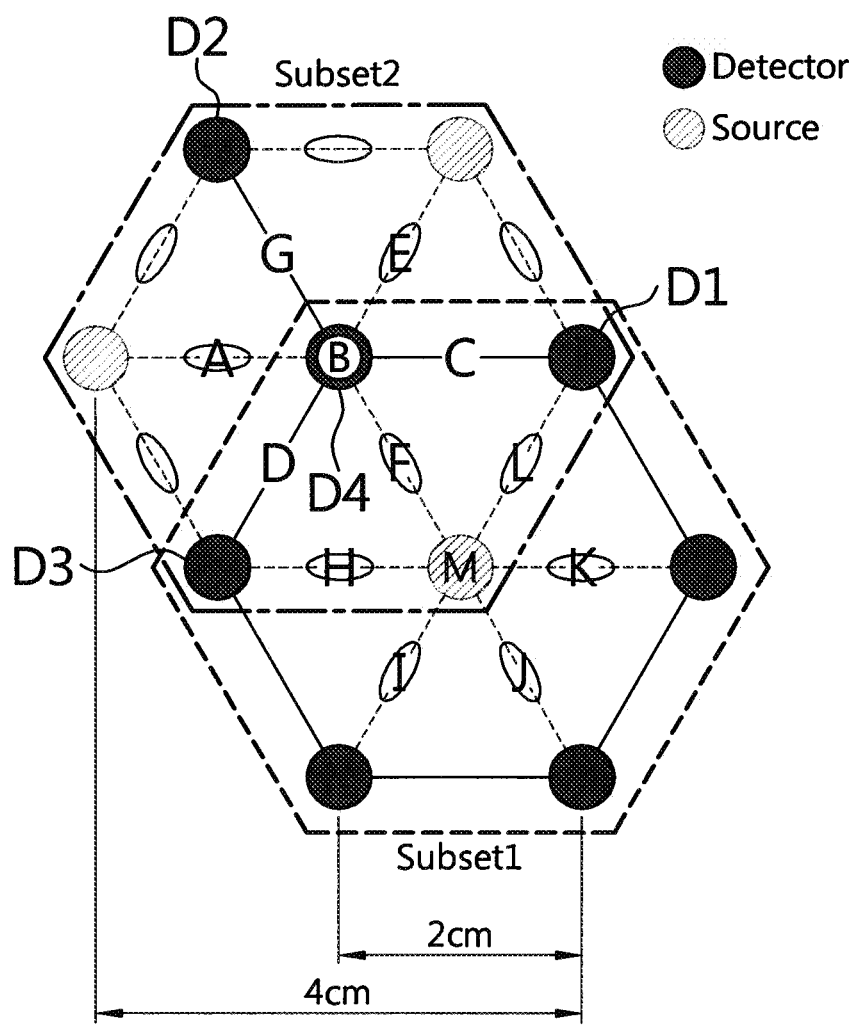
FIG. 6A shows the hemodynamics in 12 regions extracted by using conventional modulation scheme.

In the UHS, hemodynamics form only 12 regions that can be detected through conventional extraction methods, such as modulation schemes shown in FIG. 6A. FIG. 6A shows the hemodynamics in 12 regions extracted by using conventional modulation scheme.

Figure 6B:
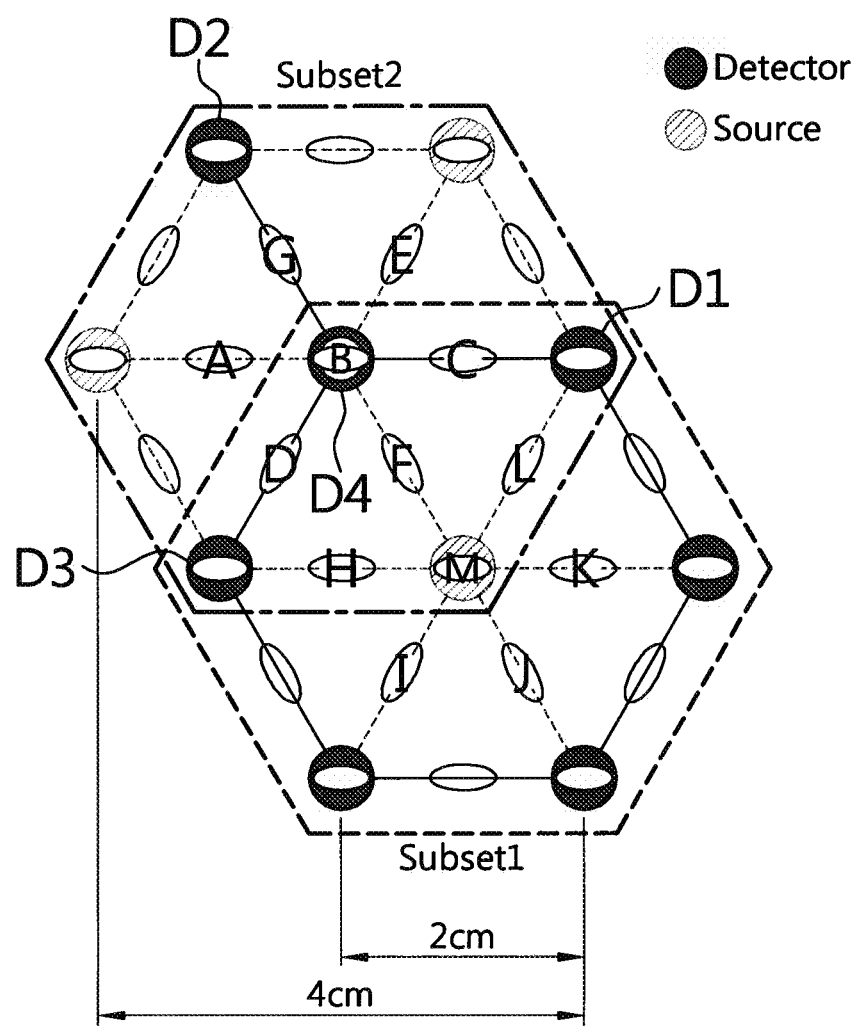
FIG. 6B shows the hemodynamics in 29 regions extracted simultaneously by using the MIMO extraction method according to an exemplary embodiment of the present invention.

However. FIG. 6B shows the hemodynamics in 29 regions extracted simultaneously by using the MIMO extraction method according to an exemplary embodiment of the present invention. Then, the spatial resolution may be improved.

D. Spatial Efficiency

A spatial efficiency may be defined as a figure of merit (FOM) of NIRS that represents the amount of resources dedicated to achieve a given spatial resolution. Since the NIRS is implemented around the human brain, increased complexity for a higher resolution diminishes the portability of the NIRS. The proposed FOM may be represented by the following Equation 16.

$$FOM = \frac{\sum_{i=1}^{n} N_{data}(i)}{Area_{total}} \times \frac{\sum_{i=1}^{n} N_{data}(i)}{N_{SD}} \quad \text{[Equation 16]}$$
$$= \frac{(33n^2 - 33n + 13)^2}{Area_{total} \times N_{SD}}$$

wherein i is the number of stages, n is the number of expanded stages. $N_{data}$ is the number of hemodynamics data at stage i (see FIG. 3A) and NSD is the total number of elements including lasers and detectors. Each numerator denotes the total number of detected points in the hexagonal SD structure. The denominator of the first term represents the skull's area and the denominator of the second term is the number of used elements. A large FOM implies (a) an increased resolution when an equal number of sources and detectors are used and (b) a lower power consumption when an identical resolution is achieved.

IV. TESTING SET UP

A. Instrument Description

Figure 7:
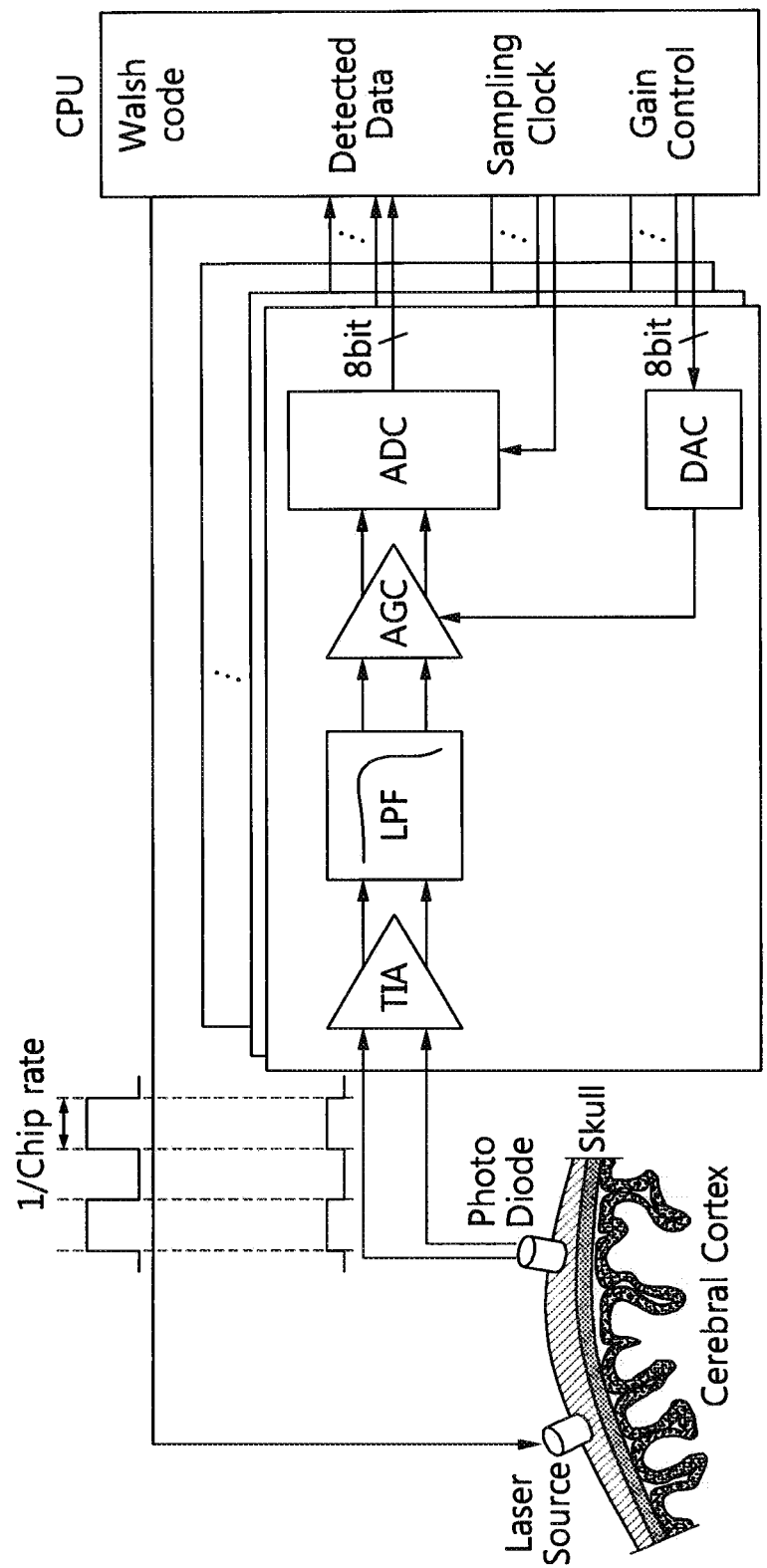
FIG. 7 shows the testing setup of the proposed NIRS according to an exemplary embodiment of the present invention.

FIG. 7 shows the testing setup of the proposed NIRS according to an exemplary embodiment of the present invention. Lasers at a wavelength of 780 nm and 850 nm with an average power of 1 mW (0 dBm) are utilized. Each laser is modulated with the Walsh code generated by a CPU for the source separation in the detector side; The code length is set to 16 and the bit rate is 200 bps. Silicon PIN diodes with the area of 7 mm2 are utilized as detectors. The current output from the photo detector is converted to a voltage signal in the TIA. Subsequent LPF and AGC adjust bandwidth and the amplitude of the voltage signal prior to the digitization. Total front-end gain is 140 dB. The resolution of the ADC is 8 bits with the sampling rate of 50 ksamples/sec. The oversampled received signal is matched filtered in the digital domain to maximize the SNR. The entire analog front-end is designed with fully differential circuits to enhance the immunity to common noise, such as ambient light. The detected signals are demodulated in the CPU for the source separation. One hexagonal SD array structure (subset 2 in FIG. 3A) is implemented for the testing of hemodynamic extraction algorithm.

B. Experiment Protocol

Figure 8:
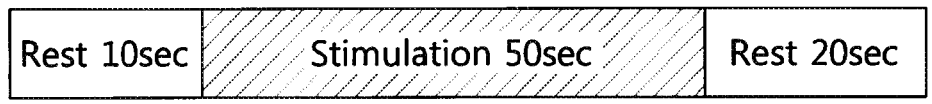
FIG. 8 shows a breath holding procedure according to an exemplary embodiment of the present invention.

The hemodynamics may be measured at the flank of subject's head with the finger tapping task. The finger tapping task included Halstead-Reitan neuropsychological battery is one of the most commonly employed tasks to study motor function of brain. The procedure for the finger tapping task is shown in FIG. 8. FIG. 8 shows a breath holding procedure according to an exemplary embodiment of the present invention.

V. MEASURE RESULTS AND METRIC COMPARISON

The detected optical signals are converted to hemodynamic responses by using the MBLL, where DPFs and absorption coefficients are obtained from. The photograph of the test setup may comprise CPU, SD Module, and Detection Circuitry. The SD array is directly attached to the frontal head without optical fibers and connected to the detection circuitry.

A. Measured Results

Figure 9:
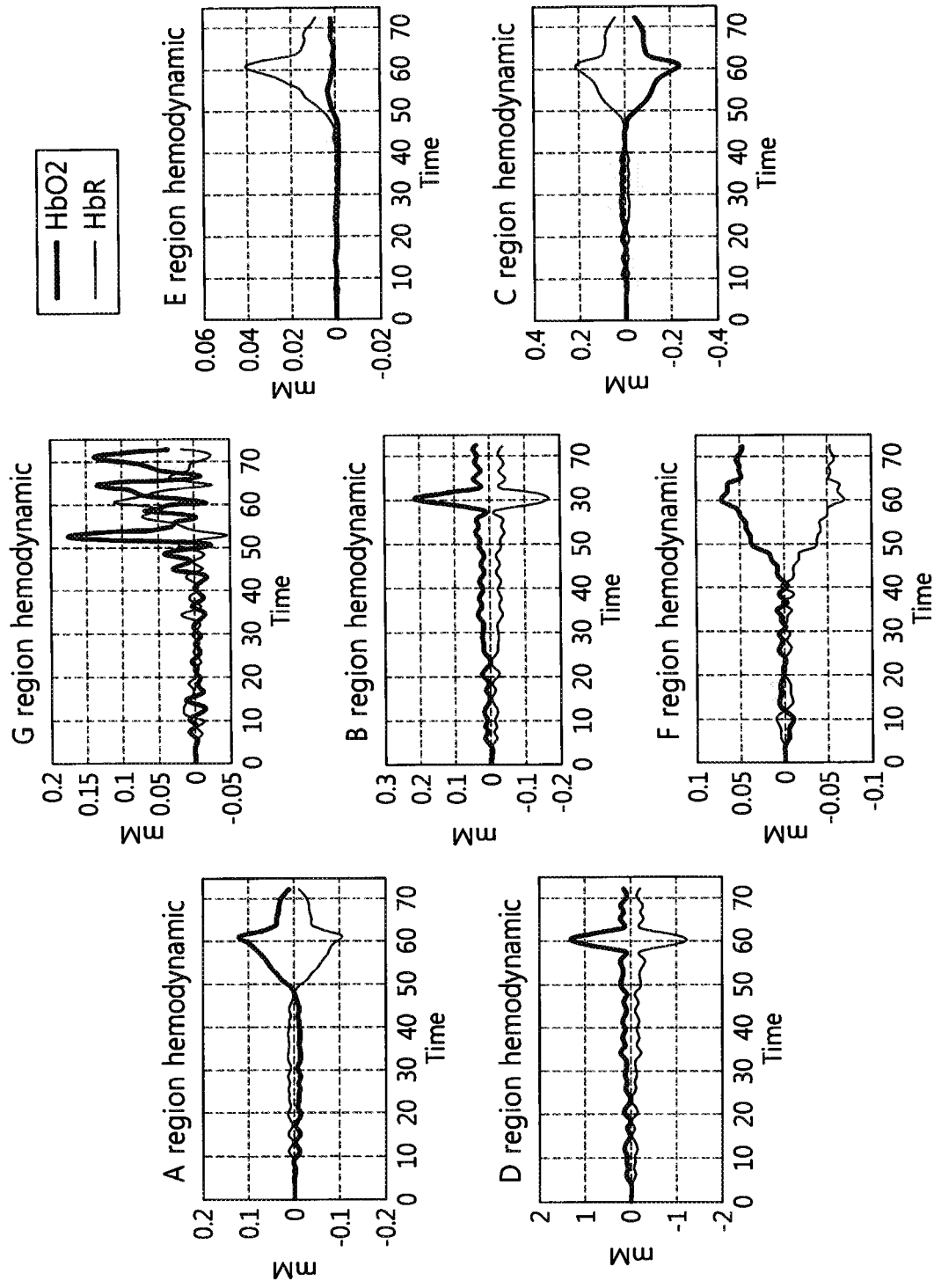
FIG. 9 shows the extracted hemodynamic responses in the subset 2 according to an exemplary embodiment of the present invention.

The measured dynamic range of the prototype NIRS system is 65 dB. Since the measured difference in the received power between lasers separated by 2 cm and 4 cm from the detector is 20 dB, the worst case SNR is 45 dB under a 4 cm SD separation. FIG. 9 shows the extracted hemodynamic responses in the subset 2 according to an exemplary embodiment of the present invention. The hemodynamics in region A. E, and F are extracted from 2 cm direct measurements. Increases in the oxyhemoglobin concentration are observed under breath holding in regions A. B. D and F as shown in FIG. 9, which coincides with the results reported in the previous research. On the contrary, oxyhemoglobin concentrations in regions C and E are decreased since neighboring regions have absorbed the oxyhemoglobin. The activation region can be determined with the increased 1 cm spatial resolution by utilizing the method proposed.

B. Metric Comparison

The area of a 9 cm-radius hemisphere modeling a human skull is 510 $cm^2$ and that of a unit UHS is 10.4 $cm^2$. We assumed that 4 stages of UHS, a total of 37 UHSs covering the area of 389 $cm^2$, are wrapping the human skull for simplicity. The following Table 5 compares the proposed method with conventional works.

TABLE 5

| Structure | Conventional model[2] | Hexagonal with Time modulation[3] | This Work |
|---|---|---|---|
| Source and Detector | 116 elements | 137 elements | 133 elements |
| Intrinsic Regions | 211 points | 268 points | 409 points |
| The metric of spatial resolution | 0.997 | 1.362 | 3.267 |
| Continuity | ○ | 3 switchings/sec | ○ |

The comparison is performed while assuming that the minimum and the maximum SD separations are 2 cm and 4 cm, respectively. Although the number of detecting points in the proposed design is similar to that of conventional hexagonal structure, the proposed structure requires fewer elements and operates continuously in time domain. As a result, the proposed method improves the FOM by 228% over a conventional rectangular structure and 140% compared to a conventional hexagonal structure.

VI. CONCLUSION

An efficient method for the extraction of hemodynamic responses is proposed. The method increases the spatial resolution of NIRS system with an efficient data extraction method. Jointly optimization in system architecture, algorithm and circuits are performed to achieve the design target. The CDMA and MIMO communication techniques are utilized. As a result, a high temporal and a spatial resolution are achieved with more than 2× FOM increment.

The exemplary embodiments according to the present invention may be recorded in computer-readable media including program instructions to implement various operations embodied by a computer. The media may also include, alone or in combination with the program instructions, data files, data structures, and the like. The media and program instructions may be those specially designed and constructed for the purposes of the present invention, or they may be of the kind well-known and available to those having skill in the computer software arts.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A near infrared spectroscopy (NIRS) system comprising:
   a plurality of sources, each of the sources configured to emit a light; and
   a plurality of detectors, each of the detectors configured to detect the light,
   wherein the sources and the detectors form a plurality of first hexagonal subsets, each of the first hexagonal subsets having one source at a center and six detectors at hexagonal vertexes, and two hexagonal vertex are shared between neighboring first hexagonal subsets.

2. The NIRS system of claim 1, wherein the sources and the detectors form a plurality of unit hexagonal subsets (UHSs), each of the UHSs having a first hexagonal subset and a second hexagonal subset, and the second hexagonal subset overlapped in a portion of the first hexagonal subset by having one detector among the six detectors at a center of the second hexagonal subset.

3. The NIRS system of claim 2, wherein hemodynamic absorption coefficients of regions between the one detector corresponding to the center of the second hexagonal subset and detectors corresponding to vertexes of the second hexagonal subset, is calculated based on variations of optical densities of lights passed through region of the center of the second hexagonal subset.

4. The NIRS system of claim 3, wherein the lights passed through region of the center of the second hexagonal subset, emitted from sources corresponding to vertexes of the second hexagonal subset.

5. The NIRS system of claim 3, wherein the variations is calculated using a photon path length corresponding to the regions where the lights passed through and a differential pathlength factor (DPF) being different according to a penetrating medium of the regions.

6. The NIRS system of claim 1, wherein the plurality of sources emit the light using code division multiple access (CDMA) scheme.

7. A data extraction method for a near infrared spectroscopy (NIRS) system, the method comprising:
first operating a plurality of sources to emit lights; and
second operating a plurality of detectors to detect the lights,
wherein the sources and the detectors form a plurality of first hexagonal subsets, each of the first hexagonal subsets having one source at a center and six detectors at hexagonal vertexes, and two hexagonal vertex are shared between neighboring first hexagonal subsets.

8. The method of claim 7, wherein the sources and the detectors form a plurality of unit hexagonal subsets (UHSs), each of the UHSs having a first hexagonal subset and a second hexagonal subset, and the second hexagonal subset overlapped in a portion of the first hexagonal subset by having one detector among the six detectors at a center of the second hexagonal subset.

9. The method of claim 8, the method further comprises,
third operating a processor to process calculation of hemodynamic absorption coefficients of regions between the one detector corresponding to the center of the second hexagonal subset and detectors corresponding to vertexes of the second hexagonal subset, based on variations of optical densities of lights passed through region of the center of the second hexagonal subset.

10. The method of claim 9, wherein the lights passed through region of the center of the second hexagonal subset, emitted from sources corresponding to vertexes of the second hexagonal subset.

11. The method of claim 9, wherein the variations is calculated using a photon path length corresponding to the regions where the lights passed through and a differential pathlength factor (DPF) being different according to a penetrating medium of the regions.

12. One or more non-transitory computer-readable storage media having stored thereon a computer program that, when executed by one or more processors causes the one or more processors to perform acts that extract a data, comprising:
first operating a plurality of sources to emit lights; and
second operating a plurality of detectors to detect the lights,
wherein the sources and the detectors form a plurality of first hexagonal subsets, each of the first hexagonal subsets having one source at a center and six detectors at hexagonal vertexes, and two hexagonal vertex are shared between neighboring first hexagonal subsets.

* * * * *